United States Patent [19]

Fujii et al.

[11] 4,288,429

[45] Sep. 8, 1981

[54] ANTIBIOTIC PLANOTHIOCINS

[75] Inventors: Tadashiro Fujii, Mishima; Satoshi Yaginuma, Shizuoka; Naoki Muto, Shizuoka; Mitsuo Hayashi, Shizuoka, all of Japan

[73] Assignee: Toyo Jozo Kabushiki Kaisha, Shizuoka, Japan

[21] Appl. No.: 175,677

[22] Filed: Aug. 5, 1980

[30] Foreign Application Priority Data

Sep. 8, 1979 [JP] Japan ............................. 54-101548
Dec. 5, 1980 [JP] Japan ............................. 55-63264

[51] Int. Cl.³ ............................................. A61K 35/00
[52] U.S. Cl. ..................................................... 424/117
[58] Field of Search ......................................... 424/117

[56] References Cited

U.S. PATENT DOCUMENTS 4,216,206  8/1980  Keller-Juslen et al. ............. 424/117

*Primary Examiner*—Jerome D. Goldberg
*Attorney, Agent, or Firm*—Young & Thompson

[57] ABSTRACT

A group of sulfur-containing antibiotics, planothiocin-A, -B, -C, -D, -E, -F and -G, are produced by culturing Actinoplanes sp. A12526 in a nutrient medium, and separating the thus-produced planothiocins therefrom. The novel antibiotics have utility in therapeutic or prophylactic antibacterial compositions or feed additives for livestock, poultry or fish.

7 Claims, 28 Drawing Figures

ANTIBIOTIC PLANOTHIOCINS

This invention relates to novel sulfur-containing antibiotic planothiocins, namely, planothiocin-A, -B, -C, -D, -E, -F and -G.

The physico-chemical properties of the planothiocins are shown in the following Table 1. The biological properties of the planothiocins are shown in Table 2.

As illustrated, planothiocins are sulfur-containing antibiotics. Among sulfur-containing antibiotics, thiostrepton, thiopeptins, sulfomycins, siomycins, A-59, pepthiomycins, thermothiocin, sporangiomycins, althiomycin, A-7413, nosiheptide, L-13365, actinothiocin, A-10947 and 35665RP are already known.

Nosiheptide has the identical amino acid composition as planothiocin-A. No antibiotics having the same amino acid composition as planothiocin-B are known. Nosiheptide has maximum absorption peaks at 416 m$\mu$ ($E_{1\ cm}^{1\%}=124$) and 440 m$\mu$ ($E_{1\ cm}^{1\%}=104.8$); however planothiocin-A has no such absorption peaks. Nosiheptide is pale yellowish crystals, whereas planothiocin-A is colorless or white crystals. The Rf values on silica gel chromatography are different in each case, i.e. Rf=0.87 on $CHCl_3$:methanol (3:1) and Rf=0.71 on ethyl acetate:methanol:water (10:2:1) for nosiheptide.

TABLE 1.

Figure 1:
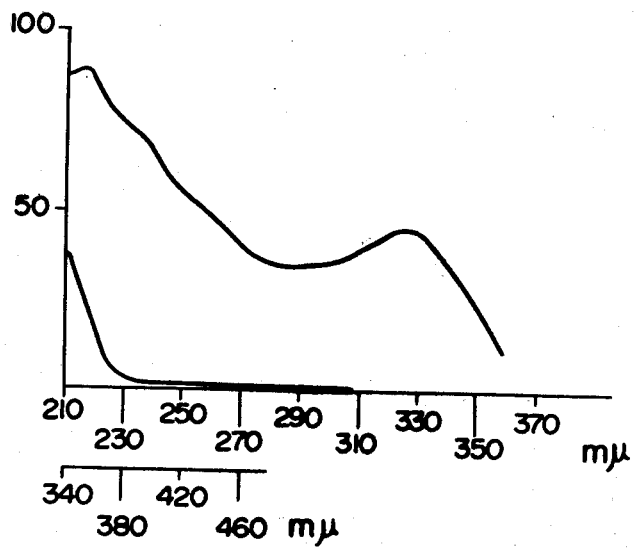
Figure 2:
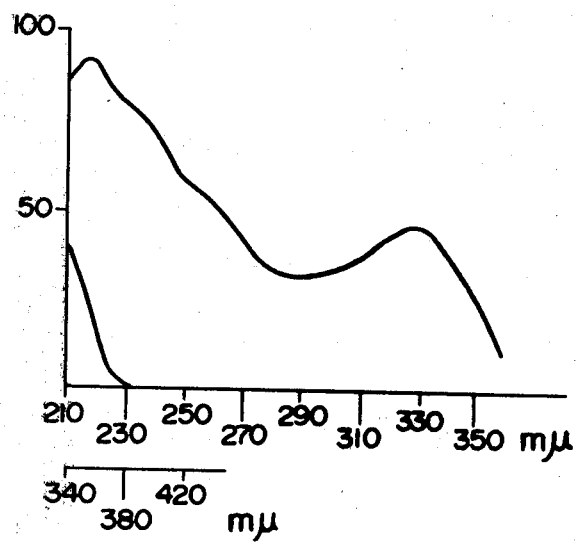
Figure 3:
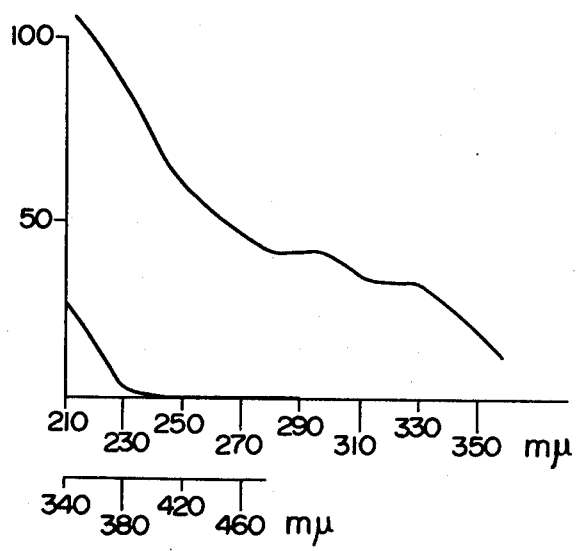
Figure 5:
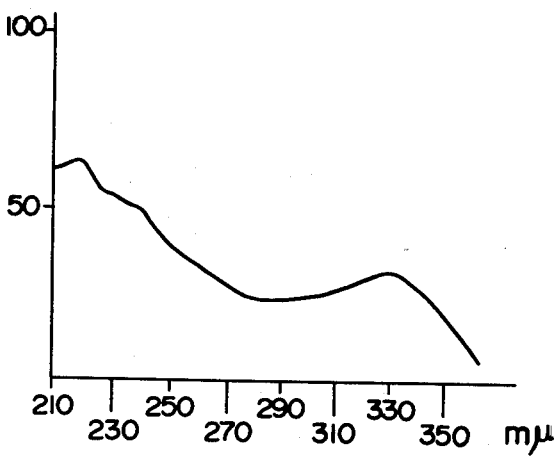
Figure 6:
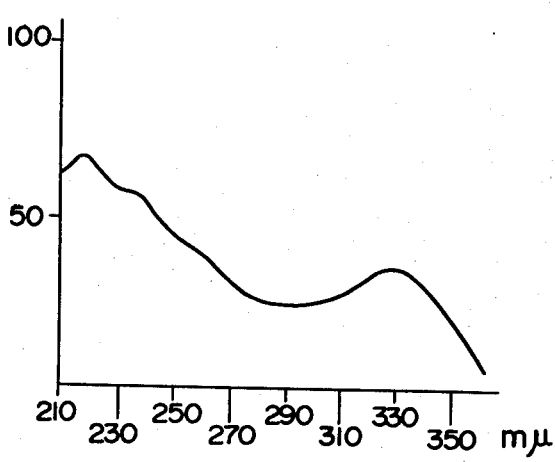
Figure 7:
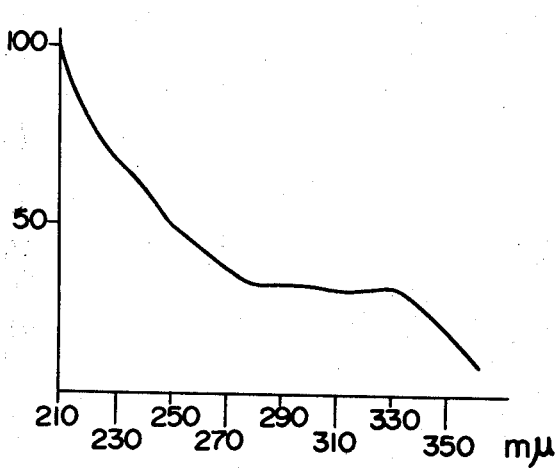

| | | Planothiocin-A | Planothiocin-B |
|---|---|---|---|
| (1) | melting point | 266–269° C. (decomp.) | 259–262° C. (decomp.) |
| (2) | elementary analysis | C = 49.47%, H = 3.3%, N = 13.25%, S = 13.73% | C = 49.37%, H = 3.45%, N = 13.30%, S = 14.19% |
| (3) | molecular weight | 1438 (minimum molecular weight by amino acid analysis; one molecule of threonine in one molecule of the compound) | 1350 (minimum molecular weight by amino acid analysis; one molecule of threonine in one molecule of the compound) |
| (4) | optical rotation | $[\alpha]_D^{23} = +19.6$ (C = 0.7, pyridine) | $[\alpha]_D^{23} = +95.4$ (C = 0.5, pyridine) |
| (5) | ultraviolet absorption spectrum (sh): shoulder ( ): $E_{1\,cm}^{1\%}$ | FIG. 1, in methanol, maximum absorption peak at 217 mμ (629.5), 239 mμ (sh)(487.7), 260 mμ (sh)(347.4), 330 mμ (317.9). FIG. 2, in acidic methanol (one drop of 0.1 N—HCl), maximum absorption peak at 219 mμ (sh)(644.9), 240 mμ (sh)(508.8), 259 mμ (sh)(371.9) 330 mμ (323.5). FIG. 3, in alkaline methanol (one drop of 0.1 N—NaOH), maximum absorption peak at 234 mμ (sh)(589.5), 299 mμ (sh)(234.2), 328 mμ (sh)(231.6). | FIG. 5, in methanol, maximum absorption peak at 218 mμ (540.4), 239 mμ (sh)(423.8), 260 mμ (sh) 294.5), 330 mμ (276.6). FIG. 6, in acidic methanol (one drop of 0.1 N—HCl), maximum absorption peak at 219 mμ (566.0), 239 mμ (sh)(468.1), 259 mμ (sh)(335.3), 331 mμ (302.1). FIG. 7, in alkaline methanol (one drop of 0.1 N—NaOH), maximum absorption peak at 239 mμ (sh), (514.0), 297 mμ (263.8), 329 mμ (262.1). |
| (6) | infrared absorption spectrum (KBr tablet) | FIG. 4; 3380, 3110, 2980, 1730, 1650, 1520, 1480, 1410, 1380, 1330, 1300, 1230, 1160, 1150, 1100, 1060, 1020, 990, 930, 910, 830, 780, 750, 700cm$^{-1}$ | FIG. 8; 3380, 3110, 2980, 1720, 1650, 1520, 1480, 1410, 1370, 1330, 1300, 1230, 1160, 1145, 1060, 1020, 990, 930, 910, 830, 780, 740, 700cm$^{-1}$ |
| (7) | color reaction | positive: decolorization of potassium permanganate, iodine. negative: ferric chloride, ninhydrin, Molisch. | positive: decolorization of potassium permanganate, iodine. negative: ferric chloride, ninhydrin, Molisch. |
| (8) | solubility | soluble: CHCl$_3$ - methanol, pyridine, DMSO, glacial acetic acid. insoluble: benzene, acetone, petroleum ether, hexane. | soluble: CHCl$_3$ - methanol, pyridine, DMSO, glacial acetic acid. insoluble: benzene, acetone, petroleum ether, hexane. |
| (9) | nature | weakly acidic | weakly acidic |
| (10) | color | white crystals (needle crystals) | white crystals (needle crystals) |
| (11) | amino acid analysis (determined by amino acid autoanalyzer, ninhydrin positive fractions of 6 N—HCl, at 105° C., for 20 hours hydrolyzate) | threonine and 2 components of ninhydrin positive. | threonine and 1 component of ninhydrin positive. |
| (11) | Rf value (silica gel-f, product of Tokyo Kasei Co.) CHCl$_3$:methanol:acetic acid (10:1:0.1) CHCl$_3$:methanol (3:1) ethyl acetate:methanol:water (10:2:1) acetonitrile:water (10:2) butanol:acetic acid:water (3:1:1) | Rf = 0.26 Rf = 0.20 Rf = 0.15 Rf = 0.43 Rf = 0.80 | Rf = 0.42 Rf = 0.27 Rf = 0.15 Rf = 0.55 Rf = 0.83 |
| (12) | stability | stable at acidic and neutral conditions. instable at alkaline condition. | stable at acidic and neutral conditions. instable at alkaline condition. |

| | | Planothiocin-C | Planothiocin-D | Planothiocin-E | Planothiocin-F | Planothiocin-G |
|---|---|---|---|---|---|---|
| (1) | melting point | 247–251° C. (decomp.) | 254–258° C. (decomp.) | 245–247° C. (decomp.) | 258–260° C. (decomp.) | 262–264° C. (decomp.) |

TABLE 1.-continued

Figure 10:
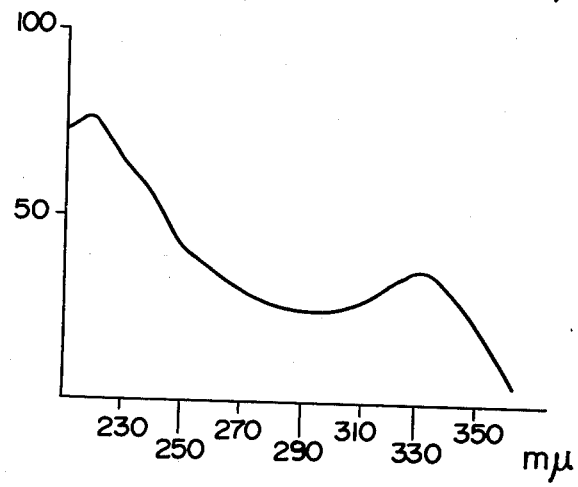
Figure 11:
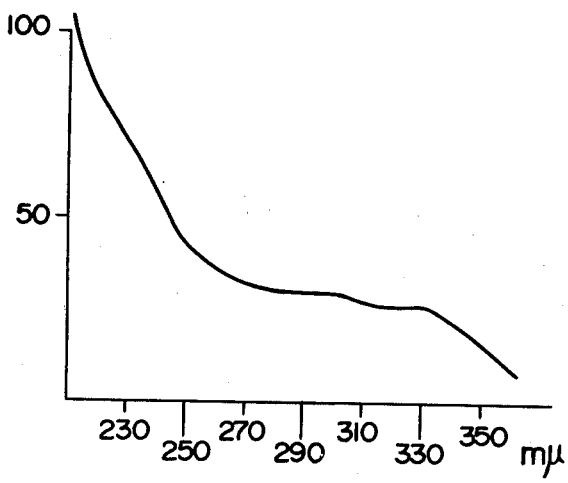
Figure 14:
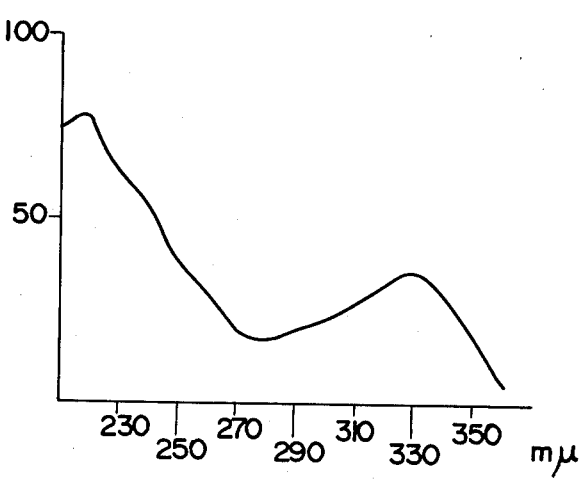
Figure 15:
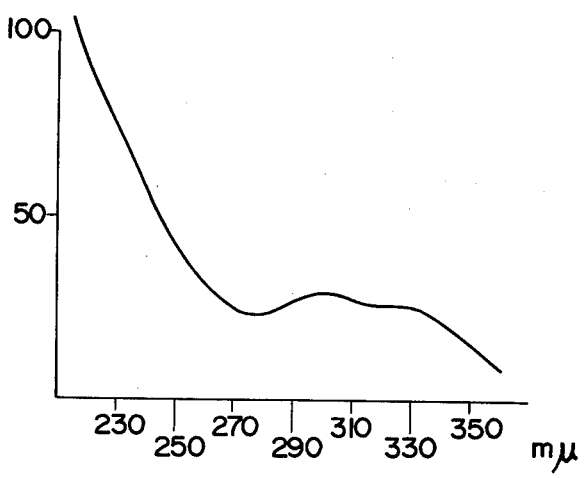
Figure 18:
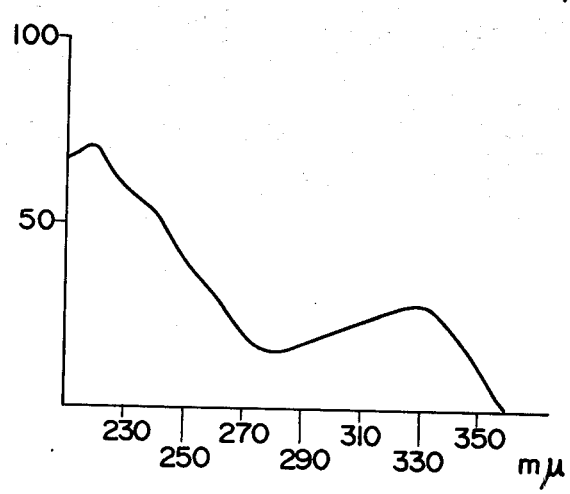
Figure 19:
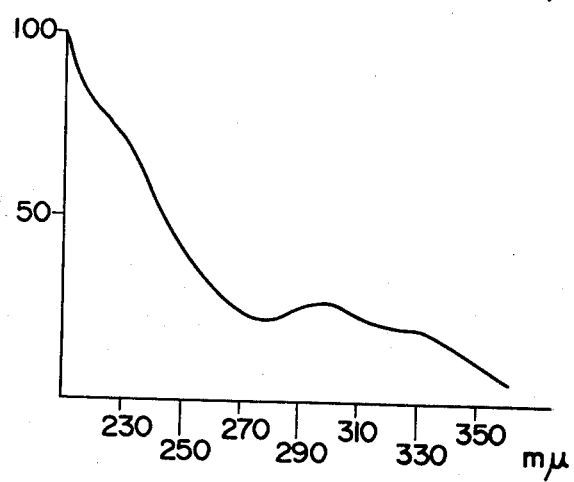
Figure 22:
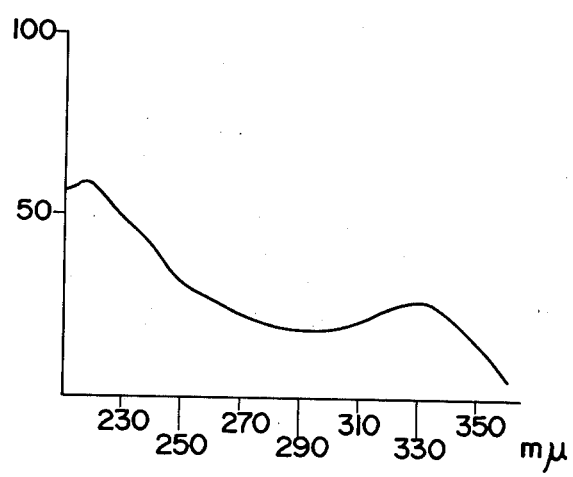
Figure 23:
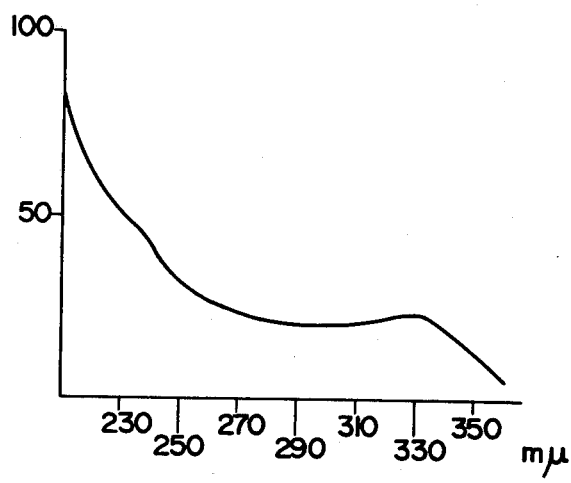
Figure 26:
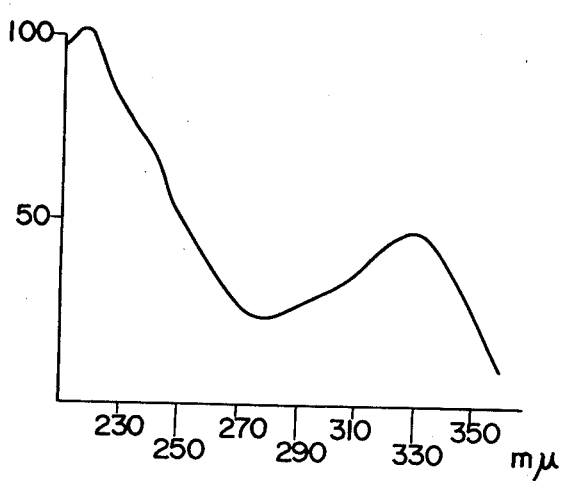
Figure 27:
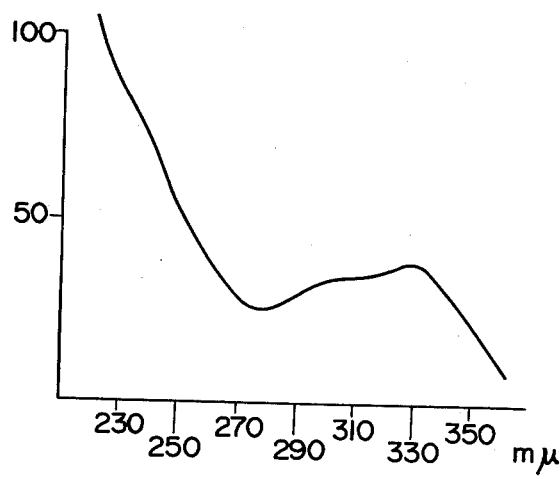

| | | | | | | | |
|---|---|---|---|---|---|---|---|
| (2) | elementary analysis | | | | | | |
| | C: | 47.81% | 48.18% | 48.31% | 49.83% | 49.26% | |
| | H: | 3.42% | 3.58% | 3.36% | 3.54% | 3.42% | |
| | N: | 13.62% | 13.26% | 13.41% | 14.70% | 13.70% | |
| | S: | 13.85% | 15.61% | 13.92% | 15.29% | 15.96% | |
| (3) | molecular weight (amino acid analysis) | 1200-1500 | 1200-1500 | 1200-1500 | 1200-1500 | 1200-1500 | |
| (4) | optical rotation [α]$_D^{20}$ (pyridine) | +2.84 (C = 0.9) | +31.4 (C = 0.7) | +45.5 (C = 0.7) | +107.8 (C = 0.8) | +122.4 (C = 0.4) | |
| (5) | ultraviolet absorption spectrum (): E$_{1\ cm}^{1\%}$ (sh): shoulder | FIG. 9, maximum absorption peak at 218 mμ (721), 240 mμ (sh) (499), 260 mμ (sh) (322), 330 mμ (sh) (327). (in methanol) | FIG. 13, in methanol, maximum absorption peak at 217 mμ (764), 240 mμ (sh) (502), 260 mμ (sh) (276), 330 mμ (sh) (343). | FIG. 17, in methanol maximum absorption peak at 217 mμ (756), 240 mμ (sh) (534), 260 mμ (sh) (308), 329 mμ (309). | FIG. 21, in methanol, maximum absorption peak at 217 mμ (744), 240 mμ (sh) (515), 260 mμ (sh) (333), 330 mμ (333). | FIG. 25, in methanol, maximum absorption peak at 217 mμ (770), 240 mμ (sh) (522), 330 mμ (350). | |
| | alkaline methanol: one drop of 0.1 N—NaOH in methanol. | FIG. 11, in alkaline methanol, maximum absorption peak at 233 mμ (sh) (611), 299 mμ (271), 329 mμ (241). | FIG. 15, in alkaline methanol, maximum absorption peak at 232 mμ (sh) (676), 300 mμ (282), 329 mμ (248) | FIG. 19, in alkaline methanol, maximum absorption peak at 233 mμ (sh) (662), 299 mμ (272), 329 mμ (207). | FIG. 23, in alkaline methanol, maximum absorption peak at 240 mμ (515), 330 mμ (291). | FIG. 27, in alkaline methanol, maximum absorption peak at 240 mμ (519), 299 mμ (247), 329 mμ (284). | |
| | acidic methanol: one drop of 0.1 N—HCl in methanol. | FIG. 10, in acidic methanol, the same as in methanol. | FIG. 14, in acidic methanol, the same as in methanol. | FIG. 18, in acidic methanol, the same as in methanol. | FIG. 22, in acidic methanol, the same as in methanol. | FIG. 26, in acidic methanol, the same as in methanol. | |
| (6) | infrared absorption spectrum (KBr tablet) | FIG. 12 3360, 3100, 1730, 1650, 1520, 1470, 1410, 1375, 1330, 1300, 1230, 1160, 1140, 1100, 1050, 1010, 980, 930, 910, 830, 780, 740cm$^{-1}$ | FIG. 16 3380, 3100, 1730, 1650, 1570, 1530, 1480, 1420, 1380, 1340, 1300, 1240, 1160, 1140, 1100, 1060, 1020, 990, 940, 910, 840, 780, 750cm$^{-1}$ | FIG. 20 3380, 3100, 1730, 1650, 1520, 1470, 1410, 1360, 1330, 1300, 1230, 1160, 1140, 1090, 1010, 980, 960, 940, 910, 830, 780, 750cm$^{-1}$ | FIG. 24 3380, 3100, 1720, 1650, 1520, 1470, 1410, 1370, 1330, 1300, 1230, 1160, 1140, 1060, 1020, 980, 960, 930, 900, 830, 780, 750cm$^{-1}$ | FIG. 28 3380, 3100, 1710, 1650, 1570, 1520, 1470, 1410, 1360, 1330, 1230, 1150, 1140, 1060, 1010, 980, 940, 910, 820, 780, 740, cm$^{-1}$ | |
| | | 3380, 3100, 1730, 1650, 1570, 1530, 1480, 1420, 1380, 1340, 1300, 1240, 1160, 1140, 1100, 1060, 1020, 990, 940, 910, 840, 780, 750cm$^{-1}$ | | 3380, 3100, 1730, 1650, 1520, 1470, 1410, 1360, 1330, 1300, 1230, 1160, 1140, 1090, 1010, 980, 960, 940, 910, 830, 780, 750cm$^{-1}$ | 3380, 3100, 1720, 1650, 1520, 1470, 1410, 1370, 1330, 1300, 1230, 1160, 1140, 1060, 1020, 980, 960, 930, 900, 830, 780, 750cm$^{-1}$ | 3380, 3100, 1710, 1650, 1570, 1520, 1470, 1410, 1360, 1330, 1230, 1150, 1140, 1060, 1010, 980, 940, 910, 820, 780, 740, cm$^{-1}$ | |
| (7) | color reaction | positive: decolorization of potassium permanganate. negative: ferric chloride, ninhydrin Molisch. | | | | | |
| (8) | solubility | soluble: CHCl$_3$, pyridine, DMF, DMSO insoluble: benzene, acetone, petroleum | | | | | |

TABLE 1.-continued

| | | | | | |
|---|---|---|---|---|---|
| (9) nature | ether, water. | 780, 750cm⁻¹ 3380, 3100, 1730, 1650, 1570, 1530, 1480, 1420, 1380, 1340, 1300, 1240, 1160, 1140, 1100, 1060, 1020, 990, 940, 910, 840, 780, 750cm⁻¹ | 750cm⁻¹ 3380, 3100, 1730, 1650, 1520, 1470, 1410, 1360, 1330, 1300, 1230, 1160, 1140, 1090, 1010, 980, 960, 940, 910, 830, 780, 750cm⁻¹ | 750cm⁻¹ 3380, 3100, 1720, 1650, 1520, 1470, 1410, 1370, 1330, 1300, 1230, 1160, 1140, 1060, 1020, 980, 960, 930, 900, 830, 780, 750cm⁻¹ | cm⁻¹ 3380, 3100, 1710, 1650, 1570, 1520, 1470, 1410, 1360, 1330, 1230, 1150, 1140, 1060, 1010, 980, 940, 910, 820, 780, 740, cm⁻¹ |
| (10) color | weakly acidic | white | | | |
| | | 3380, 3100, 1730, 1650, 1570, 1530, 1480, 1420, 1380, 1340, 1300, 1240, 1160, 1140, 1100, 1060, 1020, 990, 940, 910, 840, 780, 750cm⁻¹ | 3380, 3100, 1730, 1650, 1520, 1470, 1410, 1360, 1330, 1300, 1230, 1160, 1140, 1090, 1010, 980, 960, 940, 910, 830, 780, 750cm⁻¹ | 3380, 3100, 1720, 1650, 1520, 1470, 1410, 1370, 1330, 1300, 1230, 1160, 1140, 1060, 1020, 980, 960, 930, 900, 830, 780, 750cm⁻¹ | 3380, 3100, 1710, 1650, 1570, 1520, 1470, 1410, 1360, 1330, 1230, 1150, 1140, 1060, 1010, 980, 940, 910, 820, 780, 740, cm⁻¹ |
| (11) amino acid analysis: (determined by amino acid auto analyzer, ninhydrin positive fractions of 6 N—HCl, at 105° C., for 20 hours hydrolyzate) | threonine and two components of ninhydrin positive. | threonine and ninhydrin positive two components. | threonine and ninhydrin positive two components. | threonine and ninhydrin positive one component. | threonine and ninhydrin positive one component. |
| (12) Rf value (silica gel-f, product of Tokoyo Kasei Co.) CHCl₃:methanol:acetic acid (20:1:0.1) | Rf = 0.43 | Rf = 0.57 | Rf = 0.57 | Rf = 0.67 | Rf = 0.79 |
| ethyl acetate:methanol:acetic acid (10:1:0.2) | Rf = 0.49 | Rf = 0.41 | Rf = 0.55 | Rf = 0.65 | Rf = 0.49 |
| acetonitrile:water (10:1) | Rf = 0.42 | Rf = 0.37 | Rf = 0.49 | Rf = 0.49 | Rf = 0.41 |
| chloroform:methanol (10:1) | Rf = 0.85 | Rf = 0.87 | Rf = 0.92 | Rf = 0.92 | Rf = 0.94 |

TABLE 2.

| | planothiocin-A | planothiocin-B | planothiocin-C | planothiocin-D | planothiocin-E | planothiocin-F | planothiocin-G |
|---|---|---|---|---|---|---|---|
| acute toxicity (mice, i.p., mg/kg) | 500 (no death) | 500 (no death) | 500 (no death) | 500 (no death) | 500 (no death) | 500 (no death) | 500 (no death) |

| Minimum Inhibitory Concentration | planothiocin-A | planothiocin-B | planothiocin-C | planothiocin-D | planothiocin-E | planothiocin-F | planothiocin-G |
|---|---|---|---|---|---|---|---|
| MIC (7/ml) | | | | | | | |
| *Staphylococcus aureus* ATCC 6538p | 0.008 | 0.016 | 0.008 | 0.004 | 0.016 | 0.031 | 0.016 |
| *Staphylococcus aureus* MS353 | 0.016 | 0.031 | 0.008 | 0.004 | 0.016 | 0.031 | 0.016 |
| *Staphylococcus aureus* MS353 C36 | 0.016 | 0.031 | 0.008 | 0.004 | 0.016 | 0.031 | 0.016 |
| *Staphylococcus aureus* MS353 A0 | 0.008 | 0.031 | 0.008 | 0.004 | 0.016 | 0.031 | 0.016 |
| *Staphylococcus aureus* 0116 | 0.008 | 0.031 | 0.008 | 0.008 | 0.016 | 0.031 | 0.016 |
| *Staphylococcus aureus* 0119 | 0.008 | 0.016 | 0.008 | 0.004 | 0.016 | 0.031 | 0.016 |
| *Staphylococcus aureus* 0126 | 0.016 | 0.031 | 0.008 | 0.004 | 0.016 | 0.031 | 0.016 |
| *Staphylococcus aureus* 0127 | 0.016 | 0.031 | 0.008 | 0.008 | 0.016 | 0.031 | 0.016 |
| *Staphylococcus epidermidis* sp-al-1 | 0.031 | 0.063 | 0.016 | 0.016 | 0.063 | 0.125 | 0.016 |
| *Streptococcus pyrogenes* N.Y.5 | <0.002 | 0.004 | <0.002 | <0.002 | 0.004 | <0.002 | <0.002 |
| *Streptococcus pyrogenes* 1022 | 0.004 | 0.008 | 0.004 | 0.004 | 0.008 | 0.004 | 0.004 |
| *Streptococcus faecalis* 1501 | 0.25 | >1 | 0.5 | 1 | >1 | >1 | >1 |
| *Streptococcus agalactiae* 1020 | 0.063 | 1 | 0.25 | 1 | 1 | >1 | 0.5 |
| *Sarcina lutea* ATCC 9341 | 0.004 | 0.008 | <0.002 | <0.002 | 0.008 | 0.008 | 0.002 |
| *Micrococcus flavus* ATCC 10240 | 0.004 | 0.008 | <0.002 | <0.002 | 0.008 | 0.008 | 0.002 |
| *Corynebacterium diphtheriae* P.W.8 | 0.004 | <0.002 | <0.002 | <0.002 | 0.004 | 0.004 | 0.002 |
| *Bacillus subtilis* ATCC 6633 | 0.031 | 0.063 | 0.031 | 0.016 | 0.031 | >1 | 0.063 |
| *Escherichia coli* NIHJ-JC2 | >1 | >1 | >1 | >1 | >1 | >1 | >1 |
| *Escherichia coli* B | >1 | >1 | >1 | >1 | >1 | >1 | >1 |
| *Klebsiella pneumoniae* ATCC 10031 | >1 | >1 | >1 | >1 | >1 | >1 | >1 |
| *Salmonella typhosa* H901 | >1 | >1 | >1 | >1 | >1 | >1 | >1 |

Thus, planothiocin-A and -B are novel and not identical with other known sulfur-containing antibiotics.

Substances having the same amino acid compositions as planothiocin-C, -D and -E are nosiheptide and planothiocin-A. Also, a substance having the same amino acid composition as planothiocin-F and -G is planothiocin-B.

Comparing nosiheptide with planothiocin-C, -D and -E, nosiheptide has the characteristics mentioned hereinabove, whereas planothiocin-C, -D and -E have no absorption peaks in the visible range and are white crystals. 35665RP is a derivative of nosiheptide and has an absorption peak at 405 mμ ($E_1$ $_{cm}^{1\%}$ = 107).

The Rf values by silica gel thin layer chromatography for planothiocin-C, -D, -E, -F and -G are different from nosiheptide, and from planothiocin-A and -B, as follows:

nosiheptide:
(1)* Rf=0.35,
(2)** Rf=0.27,
(3)*** Rf=0.29,
(4)**** Rf=0.62.

planothiocin-A:
(1)* Rf=0.25,
(2)** Rf=0.13,
(3)*** Rf=0.19,
(4)**** Rf=0.05.

planothiocin-B:
(1)* Rf=0.43,
(2)** Rf=0.22,
(3)*** Rf=0.18,
(4)**** Rf=0.05.

solvent systems:
* $CHCl_3$:methanol:acetic acid = 20:1:0.1
** ethyl acetate:methanol:acetic acid = 10:1:0.2
*** acetonitrile:water = 10:1
**** $CHCl_3$:methanol = 10:1

Other physico-chemical properties such as optical rotation are different from those of known sulfur-containing antibiotics. As a result, planothiocin-C, -D, -E, -F and -G are not identical with known sulfur-containing antibiotics. Therefore, the planothiocins of the present invention are novel antibiotics.

The planothiocins-producing microogranism is Actinomycetales isolated from soil sample of paprika field in Mihama-cho, Mikata-gun, Fukui-ken, Japan, and is referred to genus Actinoplanes, and designated Actinoplanes sp. A12526. The said strain has been deposited in the Institute for Microbiological Industry and Technology, M.I.T.I., Japan as permanent deposit No. FERM-P No. 5063.

The taxonomical properties of this strain are as follows:

[I] Morphological properties:

The observations on starch-inorganic salt agar medium cultured at 30° C. for 10–14 days are as follows:

The substrate mycelium is weavy or flexuous, branched, 0.8–1.0μ in diameter, with no formation of aerail hyphae.

Sporangia are formed on the short sporangiophore that emerges from the substrate mycelium. The shapes of the sporangia are spherical or elliptical, 5–10×5–15μ in size, and contain many sporangiospores. The sporangiospores are mostly spherical or subspherical, 1–1.5μ in diameter, and motile by polytrichous flagellae.

[II] Composition of diaminopimelic acid:

Diaminopimelic acid detected by whole cell analysis is of the meso-type as a major component and hydroxy-type as a minor component.

[III] Cultural characteristics on various media:

The observation results or cultural characteristics in various media at 30° C. for 14 days culture are shown in the following Table 3. A slight formation of immature growth aerial mycelia on many media was observed.

The indication of the color is based on the "Color Harmony Manual," 4th Ed., 1958, published by Container Corporation of America.

TABLE 3

Cultural characteristics on various media

| Medium | Growth | Sporangium | Colour of substrate mycelium | soluble pigment |
| --- | --- | --- | --- | --- |
| Sucrose-nitrate agar | good | poor | light melon yellow(3ea) | none |
| Glucose-asparagine agar | poor | few | light wheat (2ea) | none |
| Glycerol-asparagine agar | few | few | colorless | none |
| Inorganic salts-starch agar | good | medium | amber (3lc) - light amber (3ic) | none |
| Tyrosine agar | poor to few | few | colorless - light ivory (2ca) | none |
| Oatmeal agar | good | poor | amber (3nc - 3lc) | none |
| Yeast-malt agar | good | poor | topaz (3ne) - cinnamon (3le) | none |
| Bennett's agar | good | few | topaz (3ne) | none |
| Emerson's agar | good | poor | amber (3pc - 3nc) | none |
| Nutrient agar | poor | none | colorless | none |
| Hickey and Tresner agar | medium | medium to poor | cork tan (4ie) | cork tan (4ie) |
| Peptone Czapeck's agar | good | medium | russet orange (4nc) | none |

[IV] Physiological properties:

The physiological properties are illustrated as follows:

(1) Utility of carbon sources:

| Carbon source | Utilization | Carbon source | Utilization |
| --- | --- | --- | --- |
| L-arabinose | + | salicin | + |
| D-xylose | + | D-galactose | + |
| D-glucose | + | glycerol | + |
| D-fructose | + | L-sorbose | − |
| D-mannose | + | trehalose | + |
| D-mannitol | + | α-melibiose | + |
| inositol | + | D-ribose | + |
| L-rhamnose | + | maltose | + |
| sucrose | + | melezitose | ± |
| β-lactose | + | D-cellobiose | + |
| raffinose | − | D-sorbitol | − |
| cellulose | − | dulcitol | − |
| starch | + | | |

(+ = positive; − = negative; ± = weakly positive)

(2) Growth temperature: 7–40° C.
(3) Peptonization and coagulation of skim milk: positive
(4) Melanin production:
   Tyrosine agar medium: negative.
   Peptone yeast iron agar medium: positive.
(5) Starch hydrolysis: positive.
(6) Cellulose decomposition: negative.
(7) Casein hydrolysis: positive.
(8) Tyrosine decomposition: positive.
(9) Gelatin liquefaction: positive.
(10) Xanthine decomposition: negative.
(11) Hypoxanthine decomposition: negative.
(12) Hydrogen sulphide formation: positive.
(13) Nitrate reduction: positive.

According to the above taxonomical data, wherein the strain A12526 has sporangia-bearing sporangiophores grown on branching substrate mycelia, spherical or elliptical shaped sporangia, spherical or subspherical sporangiospores with motile polar flagellae and meso diaminopimelic acid, this strain belongs to the genus Actinoplanes.

Planothiocins can be obtained preferably from a cultured broth of the above strain Actinoplanes sp. A12526. The above strain is only illustrative and other planothiocin-producing microorganisms can be used. For example, planothiocin-producing microorganisms belonging to genus Actinoplanes or its mutants can be used.

Planothiocins can be produced by aerobically cultivating a planothiocin-producing strain belonging to genus Actinoplanes in a conventional antibiotic-producing medium. Solid or liquid media can be used, and for industrial scale production submerged aeration culture is preferable.

A conventional nutrient medium for microorganisms can be used, containing assimilable carbon sources such as glucose, sucrose, lactose, maltose, starch, molasses or glycerol and assimilable nitrogen sources such as corn steep liquor, soybean powder, cotton seed powder, wheat gluten, peptone, meat extract, yeast extract, dry yeast, casein hydrolyzate, ammonium salt or nitrate. Phosphate, carbonate, sulfate and salts of magnesium, calcium, potassium, sodium, cobalt, ferrous or manganese can be added to the medium as required.

The cultivation temperature depends on the growth of the microorganisms and the production of planothiocins. Preferably the temperature is from 25° to 30° C.

The cultivation time depends on the conditions and is usually from 2-4 days. Cultivation is terminated when the maximum potency of planothiocins in the medium has been reached.

Planothiocins are produced mainly in the mycelia and partially in the culture filtrate.

One technique of isolating and purifying planothiocin-A, -B, -C, -D, -E, -F and -G components from mixtures of planothiocins is as follows:

Cultured wet mycelia and filtrate are obtained by filtrating or centrifuging the cultured broth of the above planothiocin-producing strain.

The culture filtrate contains a small amount of planothiocins and preferably the antibiotics can be isolated from the cultured mycelia. Planothiocins can be extracted from the wet mycelia by adding acetone. The acetone extract is concentrated in vacuo and re-extracted by adding ethyl acetate. The ethyl acetate extract is concentrated in vacuo to obtain a brownish oily syrup. A brownish precipitate is obtained by adding hexane thereto. This precipitate is dissolved in a mixture of chloroform and methanol and concentrated in vacuo to obtain a pale brownish precipitate after removing chloroform. This operation is repeated to obtain a grayish white precipitate which is a crude mixture of planothiocins containing planothiocin-A, -B, -C, -D, -E, -F and -G.

The crude product is dissolved in a mixture of chloroform and methanol (3:1) and dried by adding silica gel powder. The said mixture is subjected to silica-gel column chromatography with a developer chloroform:methanol:acetic acid (20:1:0.1).

A group of active fractions containing mainly planothiocin-F and -G; planothiocin-D and -E; planothiocin-B and -C; and planothiocin-A can be obtained.

An active fraction containing planothiocin-F and -G is concentrated in vacuo to obtain a white powder which is purified by subjecting it to silica gel column chromatography, eluting with a mixture of chloroform and methanol (25:1).

An active fraction containing planothiocin-E and -D can be purified by concentration and silica-gel column chromatography, developing with a mixture of ethyl acetate:methanol:acetic acid (20:1:0.2).

Also an active fraction containing planothiocin-B and -C can be purified by the same process hereinabove.

White crystals of planothiocin-A can be obtained by dissolving the concentrate of active fractions containing planothiocin-A in a mixture of chloroform:methanol (2:1), and removing chloroform to effect recrystallization.

The thus-obtained planothiocins can be used for therapeutic or prophylactic antibacterial compositions or feed additives for livestock, poultry or fish.

Feed additives for growth-promoting effect such as an increase of feed effect and growth effect on pigs, are preferably used at the level of 1-20 ppm of planothiocins. The growth-promoting effect on chickens can be achieved by adding 1-10 ppm of the feed additives. For fish, 0.1-100 ppm is added in the feed.

Commercially available feed can be used for adding planothiocins. For antibacterial therapeutic or prophylactic use, 1-500 ppm can be used. Feed containing planothiocins can be processed in any desired form such as mixtures, pastes, tablets, granules, pellets or syrups.

An antibacterial therapeutic or prophylactic effect, and a growth-promoting effect, were achieved by feeding the compositions to livestock, poultry or fish. Moreover an increase of spawning was observed.

Planothiocins did not remain in the organs and tissues of the livestock, poultry and fish when administered. No acute toxic symptoms or teratogenic actions were observed.

The following examples illustrate the present invention but are not to be construed as limiting.

Throughout the specification and claims, the percentages given are by weight/volume otherwise indicated except in the footnotes on Table 5.

EXAMPLE 1

A medium (pH 6.5, 100 ml) containing glucose 2%, soluble starch 2%, casein hydrolyzate 1%, yeast extract 1% and calcium carbonate 0.2% in a 500 ml-Erlenmeyer flask was sterilized at 120° C. for 20 minutes. One loopful of Actinoplanes sp. A12526 in agar slant medium was inoculated into this sterilized medium and shake cultured at 250 r.p.m., at 30° C. for 4 days. The same culture medium was prepared and cultured under the same conditions. This seed culture (200 ml in toto) was inoculated into a sterilized medium of the same composition (20 l.) in a 30 l. jar fermenter and cultured at 30° C. for 2 days at 300 r.p.m., with 20 l./min. aeration. The said cultured medium (10 l.) was inoculated into a sterilized medium containing sucrose 3%, soybean powder 2%, $CaCO_3$ 0.3%, $CoCl_2.6H_2O$ 0.001% and $MgSO_4.7H_2O$ 0.001% (pH 6.5, 200 l.) in a 250 l. tank and cultured at 30° C. for 3 days at 200 r.p.m., aeration rate 200 l./min.

The thus-obtained cultured medium was filtered after the addition of the filter-aid "Perlite" (trade name) (5 kg) to separate wet mycelia and filtrate. Antibiotics were contained both in the mycelia and in the filtrate, mainly in the mycelia.

Aceton (80 l.) was added to the wet mycelia, and the mixture was stirred vigorously for 3 hours and filtered. The acetone extract was concentrated in vacuo to 20 l. Ethyl acetate (20 l.) was added thereto, and the aqueous layer was adjusted to pH 3.0. After vigorous stirring, the ethyl acetate layer was separated. Further ethyl acetate (10 l.) was added to the residual aqueous layer, and the mixture was stirred vigorously and the ethyl acetate layer was separated. The two ethyl acetate layers were then combined. The combined organic layer (30 l.) was concentrated in vacuo to obtain a brownish oily syrup. Hexane (2 l.) was added to this syrup to precipitate a brownish substance which was collected by centrifuge. The precipitate was dissolved in a mixture (1500 ml) of chloroform and methanol (5:2) and concentrated to precipitate a pale brownish substance which was collected by centrifuge. This latter precipitate was again dissolved in the mixture of chloroform and methanol (5:2) and concentrated in vacuo to precipitate a grayish substance.

After filtration, the said substance was dried in vacuo to obtain a crude powder (15.2 g) containing planothiocin-A, -B, -C, -D, -E, -F and -G.

EXAMPLE 2

Crude powder (15 g) obtained in Example 1 was dissolved in a mixture (2 l.) of chloroform and methanol (3:1). Silica gel powder (300 g) was added to the said solution, which was then dried in vacuo to obtain a mixture with silica gel. The said silica gel mixture was added on a top of silica gel column (1500 ml) packed with a mixed solution of chloroform:methanol:acetic acid (20:1:0.1). Elution was carried out by the same solvent mixture.

Active fractions containing planothiocin components were eluted as follows:
Fractions Nos. 11-13: planothiocin-F and -G.
Fractions Nos. 14-16: planothiocin-D and -E.
Fractions Nos. 17-24: planothiocin-B and -C.
Fractions Nos. 46-60: planothiocin-A.

Active fractions Nos. 46-60 were collected and concentrated in vacuo to precipitate planothiocin-A. The precipitates were collected by centrifuge, dissolved in a mixture of chloroform:methanol (2:1) and allowed to stand at room temperature for evaporating chloroform to obtain purified planothiocin-A as white crystals (6.9 g).

EXAMPLE 3

Active fractions Nos. 11-13 containing planothiocin-F and -G were collected and concentrated in vacuo to obtain a white powder (80 mg). The powder was dissolved in a mixed solvent of chloroform and methanol (25:1) and the solution was charged on a column of silica gel (150 ml) packed with the same solvent mixture, and eluted with the same solvent.

The eluate was fractionated into fractions of 7 g each. Planothiocin-G was found in the active fractions Nos. 23-27. Planothiocin-F was found in the active fractions Nos. 30-37. Each group of active fractions was collected and concentrated in vacuo to obtain white fine needle crystals. The filtered crystals were dissolved in chloroform and allowed to stand at ambient temperature to crystallize white fine crystals of planothiocin-G and -F. The crystals of each were filtered and dried to obtain purified planothiocin-G (6 mg) and planothiocin-F (22 mg).

EXAMPLE 4

Active fractions Nos. 14–16 containing planothiocin-D and -E were collected, concentrated in vacuo and charged on a column of silica gel (150 ml) previously packed with ethyl acetate:methanol:acetic acid (20:1:0.2). Elution was carried out with the same solvent mixture (11 g/fraction). Fractions Nos. 23–29 were collected as active fractions containing planothiocin-E. Planothiocin-D was found in fractions Nos. 35–49. Each group of active fractions was concentrated in vacuo, and hexane was added thereto to precipitate planothiocin-E and -D. Each precipitate was dissolved in a mixture of chloroform:methanol (5:3), and chloroform was removed by concentration to precipitate planothiocin-E and -D as white fine needlelike crystals. The crystals were filtered and dried to obtain purified planothiocin-E (83 mg) and planothiocin-D (74 mg).

EXAMPLE 5

Active fractions Nos. 17–24 containing planothiocin-B and -C were collected, concentrated in vacuo and charged on a column of silica gel (200 ml) previously packed with ethyl acetate:methanol:acetic acid (20:1:0.2). Elution was performed by the same solvent mixture (15 g/fraction). Planothiocin-C was found in fractions Nos. 30–47 and planothiocin-B was found in fractions Nos. 70–88. Each group of active fractions was concentrated in vacuo, and hexane was added thereto to precipitate planothiocin-C and -B. Each precipitate was dissolved in a mixture of chloroform:methanol (5:3), and concentrated to remove chloroform and to precipitate white crystalline planothiocin-C and -B. The crystals were filtered and dried to yield purified planothiocin-C (137 mg) and planothiocin-B (160 mg) as white needlelike fine crystals.

EXAMPLE 6

A medium (pH 7.0, 100 ml) containing dextrin 1%, glucose 2%, soluble starch 2%, casein hydrolyzate (tradename: NZ-Amine Type A) 1%, yeast extract 1% and $CaCO_3$ 0.2% in a 500 ml-Erlenmeyer flask was sterilized at 120° C. for 20 minutes. One loopful of Actinoplanes sp. A12526 in agar slant medium was inoculated into this sterilized medium and shake cultured at 250 r.p.m. at 30° C. for 4 days. This seed culture (200 ml) was inoculated into a sterilized medium containing sucrose 3%, soybean powder 2%, $CaCO_3$ 0.3%, $CoCl_2.6H_2O$ 0.001% and $MfSO_4.7H_2$) 0.001% (20 l.) in a 30 l. jar fermenter and cultured at 30° C. for 4 days at 200 r.p.m., with 20 l./min. aeration.

The thus-obtained cultured broth was centrifuged to separate mycelia and supernatant. Acetone (10 l.) was added to the wet mycelia, and the mixture was stirred for 3 hours and filtered. The acetone extract was concentrated to 2 l., adjusted to pH 6.5, and ethyl acetate (2 l.) was added and the mixture was stirred vigorously. The ethyl acetate layer was concentrated to obtain a brownish oily syrup. Hexane (200 ml) was added to this syrup. A precipitated brownish substance was centrifuged and dissolved in a mixture of chloroform:methanol (5:1) (200 ml). This solution was concentrated to distill off the chloroform. A grayish white precipitate was collected by centrifuge and dried to yield a mixture (240 mg, purity: 60%) containing planothiocin-A and -B.

The latter mixture (170 mg) was dissolved in chloroform:methanol:acetic acid (13:1:0.1) and charged on a column of silica gel (120 ml) previously packed with the same solvent mixture. Elution was carried out with the same solvent mixture. Active fractions containing planothiocin-B were found in fractions Nos. 9–15. Planothiocin-A was found in the active fractions Nos. 16–46. Each group of fractions was collected and concentrated to precipitate white crystals which were collected by centrifuge. The crystals were dissolved in a mixture (20 ml) of chloroform:methanol (2:1) and allowed to stand at ambient temperature to remove the chloroform, whereby planothiocin-A and -B were crystallized as white needle crystals.

The thus-formed crystals were collected by filtration, and dried to obtain planothiocin-A (59 mg) and planothiocin-B (23 mg).

White needlelike crystals of planothiocin-A (50 mg) obtained by the above process were dissolved in a mixed solution (10 ml) of acetic acid:chloroform:methanol (3:1:1).

The thus-precipitated colorless prismatic crystals were collected by filtration and dried to obtain planothiocin-A as colorless prismatic crystals (29 mg).

EXAMPLE 7

A mixture of planothiocin-A and planothiocin-B (planothiocin-A:planothiocin-B=93:7) was mixed with a feed (artificial milk for piglet) comprising crude protein 22.44%, crude fat 5.14%, crude cellulose 0.74%, crude ash 6.16%, calcium 1.25% and phosphorus 0.95%, DCP (digestible crude protein) 21.38%, TDN (total digesteble nutrient) 87.41% (all percentages except for DCP and TDN are indicated by W/W).

Two groups of piglets, 10 piglets in each group, aged 25 days, were fed for 4 weeks by feeding one group with control feed (no addition of antibiotics), 0.5 ppm added feed (feed containing 0.5 ppm of antibiotics) and 5 ppm added feed, and in another group with control feed (no antibiotics feed), 10 ppm added feed (feed containing 10 ppm of antibiotics) and 20 ppm added feed.

Results of mean body weight, means body weight increase and ratio of body weight increase are shown in Table 4. As shown in the table, good growth promoting effects were observed.

TABLE 4.

| body weight | Group 1 | | |
|---|---|---|---|
| | control | 0.5 ppm added | 5 ppm added |
| initial[1] | 5.5 ± 1.08 | 5.6 ± 1.26 | 5.4 ± 1.39 |
| final[1] | 15.1 ± 2.76 | 16.2 ± 2.32 | 16.6 ± 2.15 |
| increase[2] | 9.5 ± 1.97 | 10.6 ± 1.32 | *11.2 ± 1.21 |
| ratio of increase | 100 | 110 | 118 |

| body weight | Group 2 | | |
|---|---|---|---|
| | control | 10 ppm added | 20 ppm added |
| initial[1] | 5.8 ± 1.07 | 5.8 ± 0.87 | 5.7 ± 1.15 |
| final[1] | 15.4 ± 2.14 | 17.2 ± 1.95 | 16.8 ± 2.33 |
| increase[2] | 9.7 ± 1.33 | **11.5 ± 1.27 | *11.1 ± 1.27 |
| ratio of increase | 100 | 119 | 114 |

[1] mean body weight ± standard deviation (kg).
[2] mean body weight increase ± standard deviation (kg).
** significant difference with 1% risk.
* significant difference with 5% risk.

EXAMPLE 8

A mixture of planothiocin-A and -B (ratio=93:7) was mixed with chick feed comprising crude protein 20.0%, crude fat 3.4%, crude cellulose 3.4%, crude ash 5.5%, calcium 1.03%, phosphorus 0.83% and inorganic phosphate 0.43%, TDN 70.3% and gross energy 34 Cal/1000 g.

Two grops of chickens, one male group and one female group, with 25 chickens in each group, were fed for 4 weeks by feeding with control feed (no addition of antibiotics), 0.5 ppm added feed (feed containing 0.5 ppm antibiotics), 5 ppm added feed, 10 ppm added feed and 20 ppm added feed.

As shown in Table 5, a good growth promoting effect of the present invention was observed.

In the Table, in the male group, a significant difference was observed; however, a slight characteristic dispersion value was observed in the female group.

TABLE 5.

| body weight | Female group | | | | |
|---|---|---|---|---|---|
| | control | 0.5 ppm added | 5 ppm added | 10 ppm added | 20 ppm added |
| initial[1] | 44.32 ± 2.94 | 44.12 ± 2.65 | 44.32 ± 2.48 | 44.0 ± 2.47 | 44.16 ± 2.67 |
| final[1] | 720.5 ± 60.3 | 769.6 ± 55.0 | 759.0 ± 63.2 | 787.8 ± 69.2 | 806.0 ± 53.1 |
| mean increase[2] | 676.2 ± 60.0 | **725.4 ± 54.4 | *714.7 ± 62.4 | **743.7 ± 68.5 | **761.8 ± 52.9 |

| body weight | Male group | | | | |
|---|---|---|---|---|---|
| | control | 0.5 ppm added | 5 ppm added | 10 ppm added | 20 ppm added |
| initial[1] | 44.20 ± 2.96 | 44.20 ± 3.21 | 44.48 ± 2.52 | 44.32 ± 3.16 | 44.48 ± 2.97 |
| final[1] | 784.4 ± 70.9 | 823.1 ± 46.6 | 839.2 ± 62.7 | 868.7 ± 61.6 | 863.2 ± 47.7 |
| mean increase[2] | 742.2 ± 71.1 | *778.9 ± 45.0 | **794.7 ± 63.3 | **824.4 ± 61.9 | **818.8 ± 48.6 |

[1] mean body weight ± standard deviation (g).
[2] mean body weight increase ± standard deviation (g).
*significant difference with risk 1%.
**significant difference with risk 5%.

Figure 4:
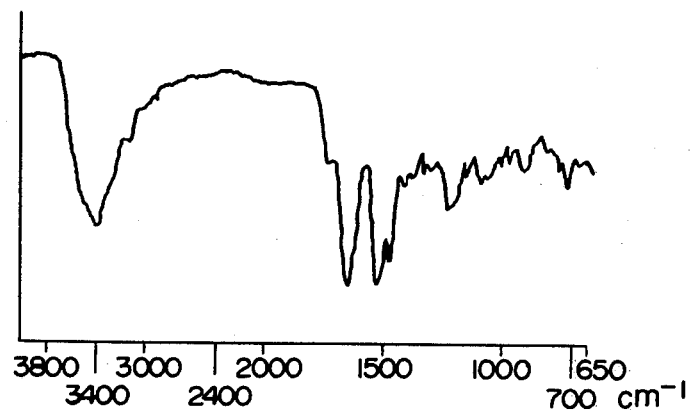

What is claimed is:

1. Planothiocin-A of the following properties:
(1) Melting point: 266°–269° C. (decomp.)
(2) Elementary analysis: C=49.47%, H=3.53%, N=13.25%, S=13.73%,
(3) Molecular weight: 1438 (minimum molecular weight calculated by amino acid analysis as one molecule of threonine in one molecule of the compound),
(4) Optical rotation: $[\alpha]_D^{23} = +19.6$ (c=0.7, pyridine)
(5) Ultraviolet absorption spectrum: FIG. 1 (in methanol), FIG. 2 (in acidic methanol), FIG. 3 (in alkaline methanol),
(6) Infrared absorption spectrum: FIG. 4,
(7) Color reaction:
positive: decoloring potassium permanganate, iodine,
negative: ferric chloride, ninhydrine, Molisch,
(8) Solubility:
soluble: mixture of CHCl$_3$-methanol, pyridine, DMSO, glacial acetic acid,
insoluble: benzene, acetone, petroleum ether, hexane,
(9) Nature: weakly acidic,
(10) Color: white crystals.

Figure 8:
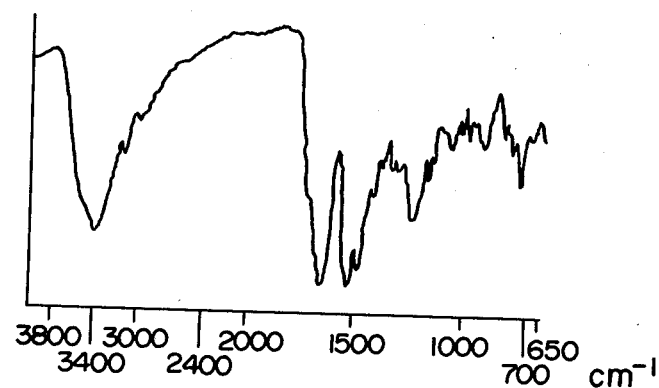
Figure 9:
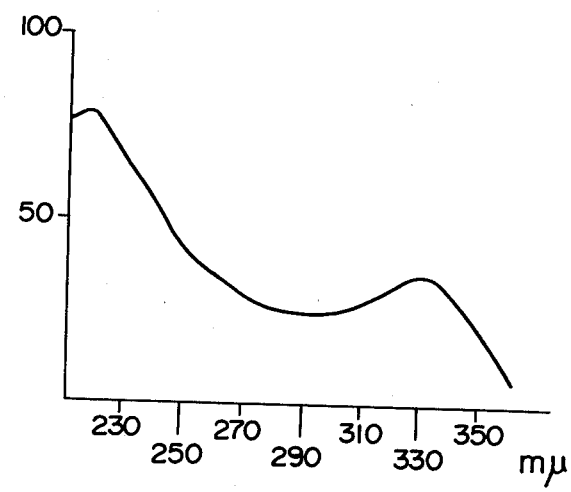
Figure 12:
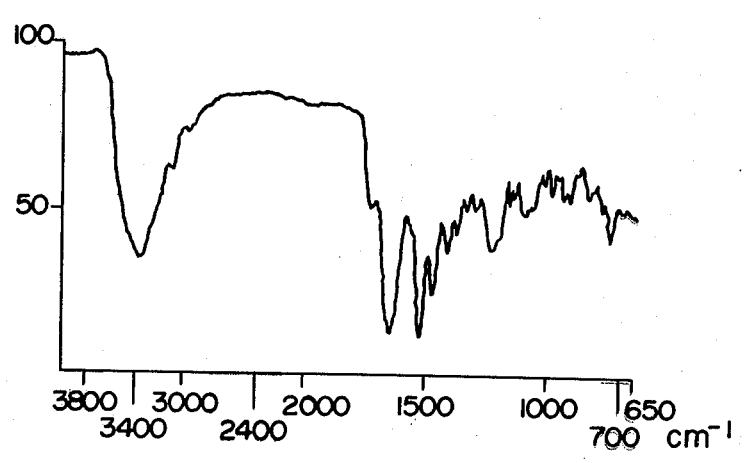

2. Planothiocin-B of the following properties:
(1) Melting point: 259°–262° C. (decomp.),
(2) Elementary analysis: C=49.37%, H=3.45%, N=13.30%, S=14.19%,
(3) Molecular weight: 1350 (minimum molecular weight calculated by amino acid analysis as one molecule of threonine in one molecule of the compound),
(4) Optical rotation: $[\alpha]_D^{23} = +95.4$ (c=0.5, pyridine),
(5) Ultraviolet absorption spectrum: FIG. 5 (in methanol), FIG. 6 (in acidic methanol), FIG. 7 (in alkaline methanol),
(6) Infared absorption spectrum: FIG. 8
(7) Color reaction:
positive: decolorization of potassium permanganate, iodine,
negative: ferric chloride, ninhydrin, Molisch,
(8) solubility:
soluble: mixture of CHCl$_3$-methanol, pyridine, DMSO, glacial acetic acid,
insoluble: benzene, acetone, petroleum ether, hexane,
(9) Nature: weakly acidic,
(10) Color: white crystals, 3. Planothiocin-C of the following properties:
(1) Melting point: 247°–251° C. (decomp.),
(2) Elementary analysis: C=47.81%, H=3.42%, N=13.62%, S=13.85%,
(3) Molecular weight: 1200–1500 (determined by amino acid analysis),
(4) Optical rotation: $[\alpha]_D^{20} = +28.4$ (c=0.9, pyridine),
(5) Ultraviolet absorption spectrum: FIG. 9 (in methanol), FIG. 11 (in alkaline methanol),
(6) Infrared absorption spectrum: FIG. 12,
(7) Color reaction:
positive: decolorization of potassium permanganate, iodine,
negative: ferric chloride, ninhydrin, Molisch,
(8) Solubility:
soluble: CHCl$_3$, pyridine, DMF, DMSO,
insoluble: benzene, acetone, petroleum ether, hexane, water,
(9) weakly acidic,
(10) Color: white crystals.

Figure 13:
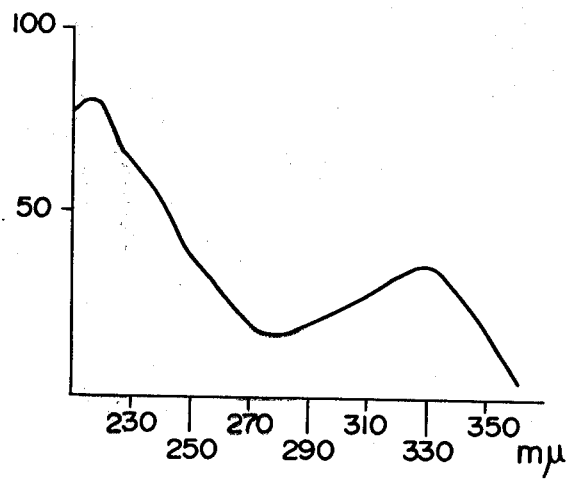
Figure 16:
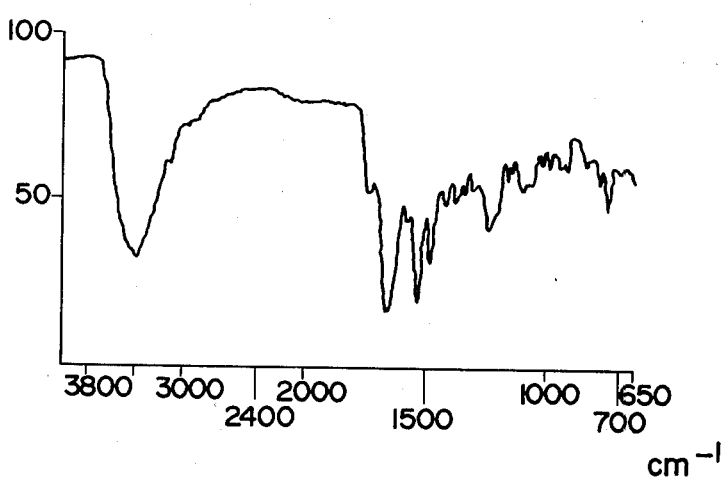

4. Planothiocin-D of the following properties:
(1) Melting point: 254°–258° C. (decomp.),
(2) Elementary analysis: C=48.18%, H=3.58%, N=13.26%, S=15.61%,
(3) Molecular weight: 1200–1500 (determined by amino acid analysis),
(4) Optical rotation: $[\alpha]_D^{20} = +31.4$ (c=0.7, pyridine).
(5) Ultraviolet absorption spectrum: FIG. 13 (in methanol), FIG. 15 (in alkaline methanol),
(6) Infrared absorption spectrum: FIG. 16,
(7) Color reaction:
positive: decolorization of potassium permanganate, iodine, negative: ferric chloride, ninhydrin, Molisch.
(8) Solubility:
soluble: CHCl₃, pyridine, DMF, DMSO,
insoluble: benzene, acetone, petroleum ether, water,
(9) Nature: weakly acidic,
(10) Color: white crystals.

Figure 17:
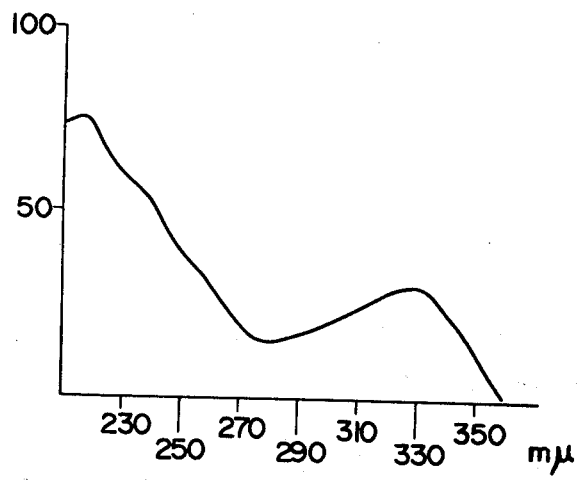
Figure 20:
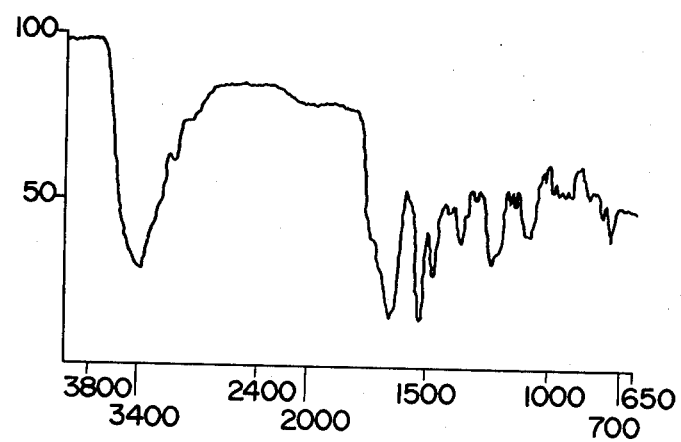

5. Planothiocin-E of the following properties:
(1) Melting point: 245°–247° C. (decomp.)
(2) Elementary analysis: C=48.31%, H=3.36%, N=13.41%, S=13.92%.
(3) Molecular weight: 1200–1500 (determined by amino acid analysis),
(4) Optical rotation: $[\alpha]_D^{20} = +45.5$ (c=0.7, pyridine),
(5) Ultraviolet absorption spectrum: FIG. 17 (in methanol), FIG. 19 (in alkaline methanol),
(6) Infrared absorption spectrum: FIG. 20,
(7) Color reaction:
positive: decolorization of potassium permanganate iodine,
negative: ferric chloride, ninhydrin, Molisch,
(8) Solubility:
soluble: CHCl₃, pyridine, DMF, DMSO,
insoluble: benzene, acetone, petroleum ether, water,
(9) Nature: weakly acidic,
(10) Color: white crystals.

Figure 21:
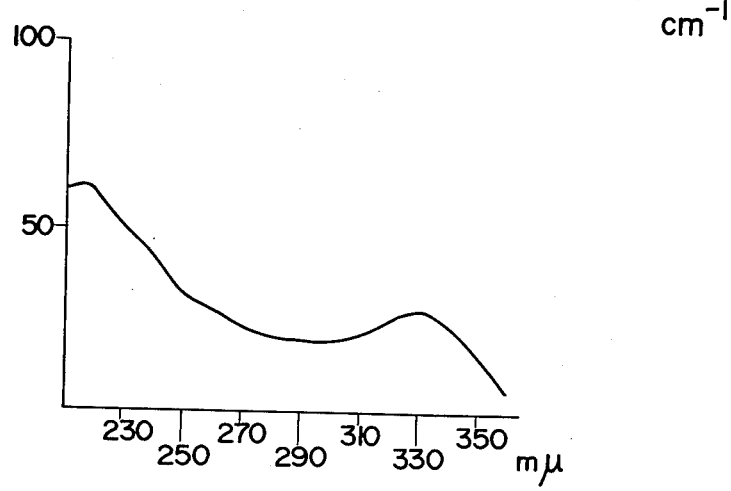
Figure 24:
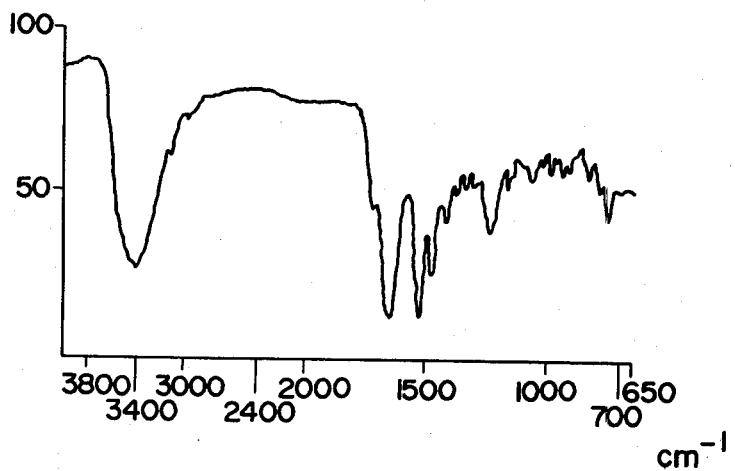

6. Planothiocin-F of the following properties:
(1) Melting point: 258°–260° C. (decomp.)
(2) Elementary analysis: C=49.83%, H=3.54%, N=14.70%, S=15.29%,
(3) Molecular weight: 1200–1500 (determined by amino acid analysis),
(4) Optical rotation: $[\alpha]_D^{20} = +107.8$ (c=0.8, pyridine),
(5) Ultraviolet absorption spectrum: FIG. 21 (in methanol), FIG. 23 (in alkaline methanol),
(6) Infrared absorption spectrum: FIG. 24,
(7) Color reaction:
positive: decolorization of potassium permanganate, iodine,
negative: ferric chloride, ninhydrin, Molisch,
(8) solubility:
soluble: CHCl₃, pyridine, DMF, DMSO,
insoluble: benzene, acetone, petroleum ether, water,
(9) Nature: weakly acidic,
(10) Color: white crystals.

Figure 25:
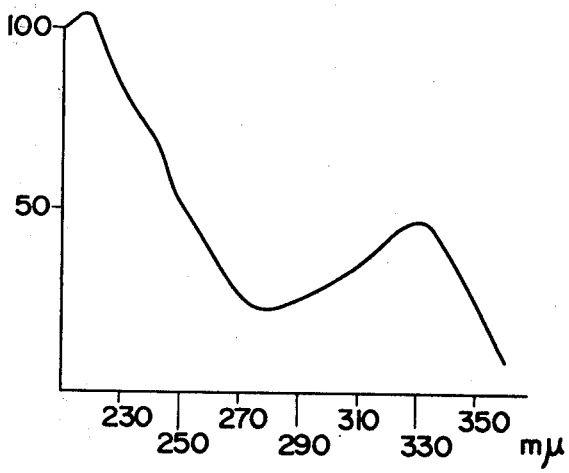
Figure 28:
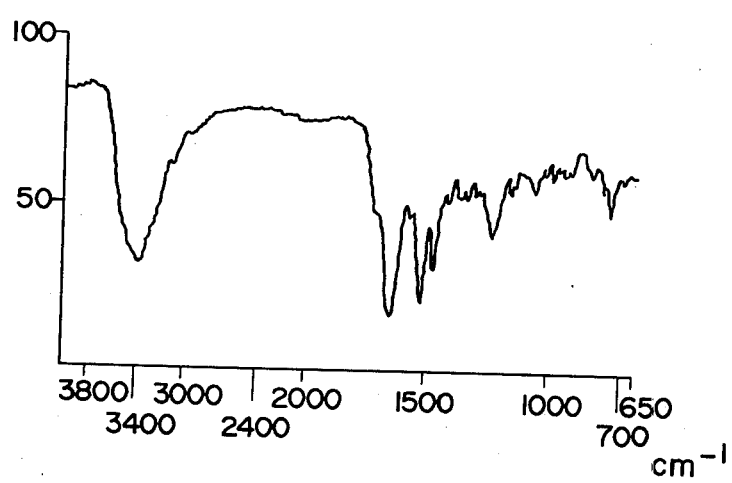

7. Planothiocin-G of the following properties:
(1) Melting point: 262°–264° C. (decomp.),
(2) Elementary analysis: C=49.26%, H=3.42%, N=13.70%, S=15.96%,
(3) Molecular weight: 1200–1500 (determined by amino acid analysis),
(4) Optical rotation: $[\alpha]_D^{20} = +122.4$ (c=0.4, pyridine),
(5) Ultraviolet absorption spectrum: FIG. 25 (in methanol), FIG. 27 (in alkaline methanol),
(6) Infrared absorption spectrum: FIG. 28,
(7) Color reaction:
positive: decolorization of potassium permanganate, iodine,
negative: ferric chloride, ninhydrin, Molisch,
(8) Solubility:
soluble: CHCl₃, pyridine, DMF, DMSO,
insoluble: benzene, acetone, petroleum ether, water,
(9) Nature: weakly acidic,
(10) Color: white crystals.

* * * * *